(12) United States Patent
Cao

(10) Patent No.: US 10,184,879 B2
(45) Date of Patent: Jan. 22, 2019

(54) OPTICAL DETECTION SYSTEMS AND METHODS OF USING THE SAME

(71) Applicant: Becton, Dickinson and Company, Franklin Lakes, NJ (US)

(72) Inventor: Jianying Cao, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 112 days.

(21) Appl. No.: 15/040,664

(22) Filed: Feb. 10, 2016

(65) Prior Publication Data

US 2016/0238511 A1  Aug. 18, 2016

Related U.S. Application Data

(60) Provisional application No. 62/117,800, filed on Feb. 18, 2015.

(51) Int. Cl.
*G01N 15/14* (2006.01)
*G01N 21/64* (2006.01)
*G01N 15/10* (2006.01)

(52) U.S. Cl.
CPC ..... *G01N 15/1434* (2013.01); *G01N 15/1459* (2013.01); *G01N 21/6486* (2013.01); *G01N 21/645* (2013.01); *G01N 2015/1006* (2013.01); *G01N 2201/062* (2013.01); *G01N 2201/068* (2013.01); *G01N 2201/06113* (2013.01); *G01N 2201/08* (2013.01)

(58) Field of Classification Search
CPC .......... G01N 15/1434; G01N 15/1459; G01N 21/645
See application file for complete search history.

(56) References Cited

U.S. PATENT DOCUMENTS

| | | | |
|---|---|---|---|
| 4,600,302 A | 7/1986 | Sage, Jr. | |
| 4,690,561 A | 9/1987 | Ito | |
| 5,125,737 A | 6/1992 | Rodriguez et al. | |
| 5,422,712 A * | 6/1995 | Ogino | G01N 15/1434 250/458.1 |
| 5,475,487 A | 12/1995 | Mariella, Jr. et al. | |
| 5,684,575 A * | 11/1997 | Steen | G01N 15/14 356/73 |

(Continued)

FOREIGN PATENT DOCUMENTS

| | | |
|---|---|---|
| EP | 0564157 A1 | 10/1993 |
| EP | 1574838 A1 | 9/2005 |

(Continued)

OTHER PUBLICATIONS

Huh et al., "Microfuildic for flow cytometric analysis of cells and particles", Physiological Measurement, 2005, vol. 26, No. 3, pp. R73-R98.

(Continued)

*Primary Examiner* — Violeta A Prieto
(74) *Attorney, Agent, or Firm* — Bret E. Field; Bozicevic, Field & Francis LLP

(57) ABSTRACT

Optical detection systems configured to collect and detect light emitted by a sample are provided. Aspects of the systems include a core region selective side scatter (SSC) collection module configured to allow for the selective detection SSC wavelength light from a core region of collected light. Also provided are methods of using the systems.

7 Claims, 3 Drawing Sheets

(56) References Cited

U.S. PATENT DOCUMENTS

| | | | |
|---|---|---|---|
| 6,813,017 B1 | 11/2004 | Hoffman et al. | |
| 7,800,754 B2* | 9/2010 | Kenyon | G01N 15/14 |
| | | | 356/337 |
| 7,990,525 B2 | 8/2011 | Kanda | |
| 8,780,338 B2* | 7/2014 | Suzuki | G01N 15/1459 |
| | | | 356/337 |
| 9,766,174 B2* | 9/2017 | Suzuki | G01N 15/1459 |
| 2003/0096302 A1* | 5/2003 | Yguerabide | C12Q 1/6816 |
| | | | 435/7.1 |
| 2009/0015831 A1* | 1/2009 | Yguerabide | C12Q 1/6816 |
| | | | 356/337 |
| 2009/0116011 A1 | 5/2009 | Kenyon | |
| 2010/0278480 A1 | 11/2010 | Vasylyev | |
| 2010/0328664 A1 | 12/2010 | Luscher | |
| 2011/0222050 A1* | 9/2011 | Suzuki | G01N 15/1459 |
| | | | 356/72 |
| 2012/0078531 A1 | 3/2012 | Lo et al. | |
| 2014/0293273 A1* | 10/2014 | Suzuki | G01N 15/1459 |
| | | | 356/73 |
| 2016/0025557 A1* | 1/2016 | Morrell | G01N 21/53 |
| | | | 356/442 |

FOREIGN PATENT DOCUMENTS

| | | |
|---|---|---|
| WO | WO2007000574 A1 | 1/2007 |
| WO | 2013101675 A2 | 7/2013 |
| WO | WO2013173446 A1 | 11/2013 |
| WO | 2014144585 A1 | 9/2014 |

OTHER PUBLICATIONS

Lee et al., "Micro flow cytometers with buried SU-8/SOG optical waveguides", Sensors and Actuators A: Physical, 2003, vol. 103, No. 1, pp. 165-170.

* cited by examiner

OPTICAL DETECTION SYSTEMS AND METHODS OF USING THE SAME

CROSS-REFERENCE TO RELATED APPLICATIONS

This application claims priority to U.S. Provisional Patent Application Ser. No. 62/117,800 filed Feb. 18, 2015, the disclosure of which application is incorporated herein by reference.

INTRODUCTION

Flow cytometry is a technique used to characterize and sort biological material, such as cells of a blood sample or particles of interest in any type of biological or chemical sample. The technique may be used to record distributions or physically sort the biological material.

A flow cytometer typically includes a sample reservoir for receiving a fluid sample, and a sheath reservoir containing a sheath fluid. The flow cytometer transports the particles (including cells) in the fluid sample as a cell stream to a flow cell, while also directing the sheath fluid to the flow cell. Within the flow cell, a liquid sheath is formed around the cell stream to impart a substantially uniform velocity on the cell stream. The flow cell hydrodynamically focuses the cells within the stream to pass through an interrogation point where light is directed onto the sample (e.g., laser light). As components of the flow stream move through the light at the interrogation point, light from the constituents of the flow stream are emitted and scattered (in the detection zone). This light is collected and imaged, e.g., using an optical lens assembly, and conveyed to a detector. Variations in the materials, such as morphologies or fluorescent labels, cause variations in the observed light that allow for characterization by collecting the light onto one or more optical detectors.

Many optical detection systems in flow cytometer platforms use a combination of an objective lens assembly and a multi-mode optical fiber light conveyor (which conveys objective lens imaged collected light to one or more detectors) for both fluorescence and side scatter (SSC) wavelength light collection. In most platforms, the diameter of the light-collecting core of an optical fiber is significantly larger than the image generated by the objective lens assembly, leading to the detection of background light (or noise). For the measurement of SSC wavelength light, this noise can impede detecting sub-cellular sized particles (e.g., sub-micron sized particles) in a sample. However, due in part to the chromatic aberration observed with imaging multiple different wavelengths of light with an objective lens, reducing the size of the light collecting core of optical fiber light conveyor to address the noise for one collected wavelength of light (e.g., an SSC wavelength) results in a reduction of the image signal in another wavelength of light (e.g., a fluorescence wavelength).

SUMMARY

Optical detection systems configured for collecting and detecting light emitted by a sample are provided. Aspects of the systems include a core region selective side scatter (SSC) collection module configured to allow for the selective detection SSC wavelength light from a core region of collected light. The inclusion of a core region selective SSC collection module in an optical detection system provides for improved detection of sample components, including sub-micron sized particles.

In certain aspects, the present disclosure provides optical detection systems that include: a light collection system configured to produce objective lens imaged collected light from a detection zone of a flow cell; a light dispersion module configured to separate the objective lens imaged collected light into at least two wavelengths of light; a first detector configured to detect a first of the at least two wavelengths of light and a second detector configured to detect a second of the at least two wavelengths of light, where the first wavelength of light is SSC wavelength light; and an aperture positioned between the light collection system and the light dispersion module, where the aperture includes an optical mask configured to selectively block SSC wavelength light from the objective lens imaged collected light that is outside of a core region from reaching the first detector. In certain embodiments, the aperture has a diameter ranging from 50μ to 500μ to match the core region. In certain embodiments, the optical mask does not block passage of at least one non-SSC wavelength light. In certain embodiments, the non-SSC wavelength light is light that is emitted from a particle in the flow stream. In certain embodiments, the optical detection system, further includes a fiber optic light conveyer positioned between the aperture and the light dispersion module, where the fiber optic light conveyor is configured to convey objective lens imaged collected light that has passed through the aperture to the light dispersion module. In certain embodiments, the detector includes a photodiode based light detector or a photomultiplier tube (PMT). In certain embodiments, the fiber optic light conveyor includes a core that has a diameter that is larger than the core region.

In certain aspects, the present disclosure provides optical detection systems that include: a light collection system configured to produce objective lens imaged collected light from a detection zone of a flow cell; a detector configured to receive the objective lens imaged collected SSC wavelength light; an optical filter configured to produce at least a first path and a second path of objective lens imaged collected light, where the first path includes at least a portion of the SSC wavelength light from the objective lens imaged collected light, and where the first path is transmitted to the detector; and an aperture configured to block passage of SSC wavelength light in the first path that is outside of a core region from reaching the detector. In certain embodiments, the first path includes from 50 to 99% of the collected SSC wavelength light. In certain embodiments, the optical detection system further includes: a light dispersion module configured to separate the second path of objective lens imaged collected light into at least two wavelengths of light; and a second detector configured to detect a first of the at least two wavelengths of light and a third detector configured to detect a second of the at least two wavelengths of light. In certain embodiments, the aperture has a diameter ranging from 50μ to 500μ to match the core region. In certain embodiments, the second path includes at least one non-SSC wavelength light. In certain embodiments, the non-SSC wavelength light is light that is emitted from a particle in the flow stream. In certain embodiments, the optical detection system further includes a fiber optic light conveyer positioned between the aperture and the detector, where the fiber optic light conveyor is configured to convey objective lens imaged collected light that has passed through the aperture to the detector. In certain embodiments, the fiber optic light conveyor includes a core that has a diameter that is larger than the core region. In certain embodiments, the aperture is attached directly to the fiber optic light conveyor. In certain embodiments, the aperture is attached directly to the detector. In certain embodiments, the optical filter is configured to reflect the objective lens imaged collected light to produce the first path. In certain embodiments, the optical filter is configured to pass the objective lens imaged collected light to produce the first path.

In certain aspects, the present disclosure provides optical detection systems that include: a light collection system configured to produce objective lens imaged collected light from a detection zone of a flow cell; a detector configured to receive the objective lens imaged collected SSC wavelength light; an optical filter configured to produce at least a first path and a second path of objective lens imaged collected light, where the first path includes at least a portion of the SSC wavelength light from the objective lens imaged collected light, and where the first path is transmitted to the detector; and a fiber optic light conveyer configured to selectively transmit SSC wavelength light in the first path from a core region of the SSC wavelength light to the detector. In certain embodiments, the first path includes from 50 to 99% of the collected SSC wavelength light. In certain embodiments, the optical detection system further includes: a light dispersion module configured to separate the second path of objective lens imaged collected light into at least two wavelengths of light; and a second detector configured to detect a first of the at least two wavelengths of light and a third detector configured to detect a second of the at least two wavelengths of light. In certain embodiments, the light transmitting core of the fiber optic light conveyer has a cross-sectional diameter ranging from 50µ to 500µ to match the core region. In certain embodiments, the second path includes at least one non-SSC wavelength light. In certain embodiments, the non-SSC wavelength light is light that is emitted from a particle in the flow stream. In certain embodiments, the detector includes a photodiode based light detector or a photomultiplier tube (PMT). In certain embodiments, the optical filter is configured to reflect the objective lens imaged collected light to produce the first path. In certain embodiments, the optical filter is configured to pass the objective lens imaged collected light to produce the first path.

In certain aspects, the present disclosure provides flow cytometers that include: a light source; a flow cell including a detection zone; and an optical detection system as set forth above (and elsewhere herein).

In certain aspects, the present disclosure provides methods of analyzing a flow stream that include: irradiating a flow stream with a light source; generating objective lens imaged light collected from a detection zone of the irradiated flow stream; and passing the objective lens imaged collected light through an aperture to a light dispersion module, where: (i) the aperture includes an optical mask that selectively blocks side scatter (SSC) wavelength light outside of a core region from passing through; and (ii) the light dispersion module is configured to separate the objective lens imaged collected light into at least a first and a second wavelength of light, where the first wavelength of light is SSC wavelength light; and detecting the first and second wavelengths of light to analyze the flow stream. In certain embodiments, the aperture has a diameter ranging from 50µ to 500µ to match the core region. In certain embodiments, the aperture has a diameter ranging from 200µ to 400µ in diameter to match the core region. In certain embodiments, the optical mask does not block passage of at least one non-SSC wavelength of light. In certain embodiments, the non-SSC wavelength of light is light that is emitted from a particle in the flow stream. In certain embodiments, the method further includes transmitting the objective lens imaged light passed through the aperture by a fiber optic light conveyer to the light dispersion module.

In certain aspects, the present disclosure provides methods of analyzing a flow stream that include: irradiating a flow stream with a light source; generating objective lens imaged light collected from a detection zone of the irradiated flow stream; directing the objective lens imaged collected light onto an optical filter configured to produce at least a first path and a second path of objective lens imaged collected light, where the first path includes at least a portion of the SSC wavelength light from the objective lens imaged collected light; and transmitting the first path of collected SSC wavelength light through a fiber optic light conveyer configured to selectively transmit a core region of the of SSC wavelength light in the first path to a detector; to analyze the flow stream. In certain embodiments, the light transmitting core of the fiber optic light conveyer has a cross-sectional diameter ranging from 50µ to 500µ to match the core region. In certain embodiments, the optical filter is configured to reflect the objective lens imaged collected light to produce the first path. In certain embodiments, the e optical filter is configured to pass the objective lens imaged collected light to produce the first path. In certain embodiments, the first path includes from 50 to 99% of the collected SSC wavelength light. In certain embodiments, the SSC wavelength light that is in the second path of collected SSC wavelength light is detected by a second detector. In certain embodiments, the detector includes a photodiode based light detector or a photomultiplier tube (PMT). In certain embodiments, the second path includes at least one non-SSC wavelength light, where the method further includes detecting the at least one non-SSC wavelength of light. In certain embodiments, the non-SSC wavelength light is light that is emitted from a particle in the flow stream.

In certain aspects, the present disclosure provides methods of analyzing a flow stream that include: irradiating a flow stream with a light source; generating objective lens imaged light collected from a detection zone of the irradiated flow stream; directing the objective lens imaged collected light onto an optical filter configured to produce at least a first path and a second path of objective lens imaged collected light, where the first path includes at least a portion of the SSC wavelength light from the objective lens imaged collected light; and passing the first path of collected SSC wavelength light through an aperture to a detector, where the aperture blocks side scatter (SSC) wavelength light outside of a core region from passing through; to analyze the flow stream. In certain embodiments, the aperture has a diameter ranging from 50µ to 500µ to match the core region. In certain embodiments, the optical filter is configured to reflect the objective lens imaged collected light to produce the first path. In certain embodiments, the optical filter is configured to pass the objective lens imaged collected light to produce the first path. In certain embodiments, the first path includes from 50 to 99% of the collected SSC wavelength light. In certain embodiments, the SSC wavelength light that is in the second path of collected SSC wavelength light is detected by a second detector. In certain embodiments, the detector includes a photodiode based light detector or a photomultiplier tube (PMT). In certain embodiments, the second path includes at least one non-SSC wavelength light, where the method further includes detecting the at least one non-SSC wavelength of light. In certain embodiments, the non-SSC wavelength light is light that is emitted from a particle in the flow stream. In certain embodiments, the method further includes transmitting the first path of light that has passed through the aperture by a fiber optic light conveyer to the detector. In certain embodiments, the aperture is attached directly to the fiber optic light conveyor. In certain embodiments, the aperture is attached directly to the detector. Additional aspects and embodiments of the disclosure are set forth below.

BRIEF DESCRIPTION OF THE FIGURES

Aspects of the disclosure may be best understood from the following detailed description when read in conjunction with the accompanying drawings.

Included in the drawings are the following figures.

DETAILED DESCRIPTION

Figure 1A:
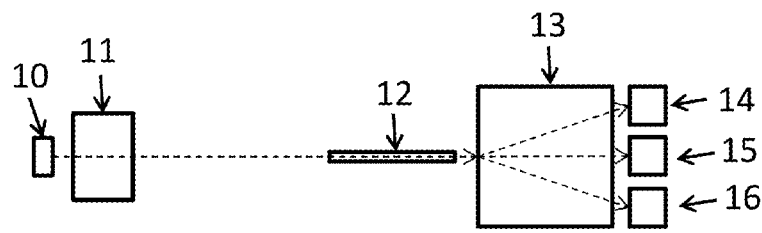
FIG. 1A illustrates an example of an optical detection system including the following elements: 10 flow cell with a detection zone; 11 objective lens assembly; 12 fiber optic light conveyor; 13 light dispersion module; 14 first fluorescence wavelength light detector; 15 second fluorescence wavelength light detector; 16 SSC wavelength light detector. The light path is represented by the dotted arrows.

Optical detection systems configured for collecting and detecting light emitted by a sample are provided. Aspects of the systems include a core region selective side scatter (SSC) collection module configured to allow for the selective detection SSC wavelength light from a core region of collected light. The inclusion of a core region selective SSC collection module in an optical detection system provides for improved detection of sample components, including sub-micron sized particles.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Optical Detection Systems

As summarized above, optical detection systems configured for collecting and detecting light emitted by a sample are provided. Aspects of the systems include a core region selective side scatter (SSC) collection module. Core region SSC collection modules as described herein are configured to allow for the selective detection SSC wavelength light from a core region of collected light. In some embodiments, the inclusion of a core region selective SSC collection module in an optical detection system provides for improved detection of sample components, including sub-micron sized particles.

Optical detection systems that include a core region SSC collection module as described herein find use in improving the signal-to-noise ratio in SSC detection as compared currently available systems. This allows, for example, for an improvement in the detection of sub-cellular sized particles, e.g., particles that are in the sub-micron size range. In certain embodiments, the optical detection system is configured to provide for dual SSC detection, which allows for simultaneous detection and analysis of both cells and sub-cellular sized particles. Examples of such embodiments are now described in greater detail below.

FIG. 1A provides a schematic of a general optical detection system that includes a flow cell having a detection zone (10), objective lens assembly (11) for producing imaged collected light from the detection zone, and a light conveyor (12) that conveys collected light to a light separation module (13) and detectors one or more detectors (shown as 14, 15, and 16 in FIG. 1A). The light path is represented by the dotted arrows. In this figure, detectors 14 and 15 represent fluorescence wavelength detectors (for two different wavelengths) and detector 16 represents a detector of SSC wavelength light.

Figure 1B:
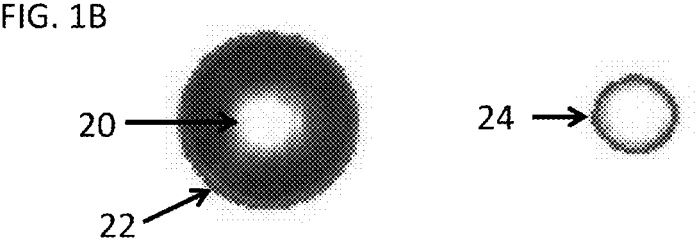
FIG. 1B. The left panel illustrates the core image size of objective lens collected light (20) which is smaller than the size of the surface of a light conveying element (or surface of a light detector)(22). The right panel illustrates a light conveyor (or detector) having a light receiving surface that is configured to be the approximate size of the core image (24), thereby preventing non-core light from being detected.

In optical detection systems, the image size of objective lens collected light (see FIG. 1B, 20) may be significantly smaller than the size of the surface of a light conveying element of the system which conveys the collected light to a detector (FIG. 1B, 22), e.g., the core of a fiber optic light conveyor. (Suitable fiber optics protocols propagating light to the active surface of the detector include, but is not limited to, flow cytometer fiber optics protocols such as those described in U.S. Pat. No. 6,809,804, the disclosure of which is herein incorporated by reference.) For example, certain optical detection systems include a light collecting system that produces images of about 200 microns in diameter (also referred to as the "core region") while the core diameter of a fiber optic light conveyor is about 800-microns. This difference in size allows for significant amounts of collected background SSC wavelength light to be conveyed to the detector, thereby reducing the signal-to-noise ratio. Thus, eliminating or reducing the detection of non-core region imaged SSC wavelength light in an optical detection system will significantly reduce optical noise without affecting detection efficiency (represented in FIG. 1B, 24).

As detailed below, core region selective SSC collection modules can include one or more elements that alone or in combination allow for selective detection of the core region of objective lens imaged collected SSC wavelength light selected from: one or more apertures having an optical mask that selectively blocks passage of SSC light that is outside of the core region, one or more optical filters, one or more light conveying elements, one or more detectors, and any combination thereof. Representative embodiments are provided below.

In certain embodiments, an optical detection system is provided that includes a light collection system configured to produce objective lens imaged collected light from a detection zone of a flow cell, a detector configured to receive the objective lens imaged collected light, and an aperture positioned between the light collection system and the detector, where the aperture includes an optical mask configured to block SSC wavelength light from the objective lens imaged collected light that is outside of a core region from reaching the detector. In other words, the aperture has a size (defined by the optical mask) that is matched to the core region of the objective lens imaged collected light.

The light collection system of the disclosed optical detection systems may be configured in any convenient manner. In certain aspects, the light collection system includes one or more objective lenses, which may include one or a combination of a collimating lens, a focusing lens, a magnifying lens, a de-magnifying lens, or other lens, that are configured to receive light from a detection zone of a flow cell and produce imaged light that is transmitted to one or more detectors in the system. Any convenient light collection systems configured to produce objective lens imaged collected light from a detection zone of a flow cell can be used. Examples of light collection systems that may be employed include those described in U.S. Pat. Nos. 3,960,449; 4,347,935; 4,667,830; 5,245,318; 5,464,581; 5,483,469; 5,602,039; 5,643,796; 5,700,692; 6,372,506 and 6,809,804; the disclosures of which are herein incorporated by reference.

In certain embodiments, the core region of the objective lens imaged collected SSC wavelength light has a diameter ranging from 50 microns($\mu$) to 500$\mu$, including form 70$\mu$ to 450μ, form 70μ to 400μ, form 100μ to 400μ, form 200μ to 400μ, etc. As such, in certain embodiments, the core region has a diameter of or about 500μ, of or about 475μ, of or about 450μ, of or about 425μ, of or about 400μ, of or about 375μ, of or about 350μ, of or about 325μ, of or about 300μ, of or about 275μ, of or about 250μ, of or about 225μ, of or about 200μ, of or about 175μ, of or about 150μ, of or about 125μ, of or about 100μ, of or about 75μ, of or about 50μ, or anywhere in between.

Figure 1C:
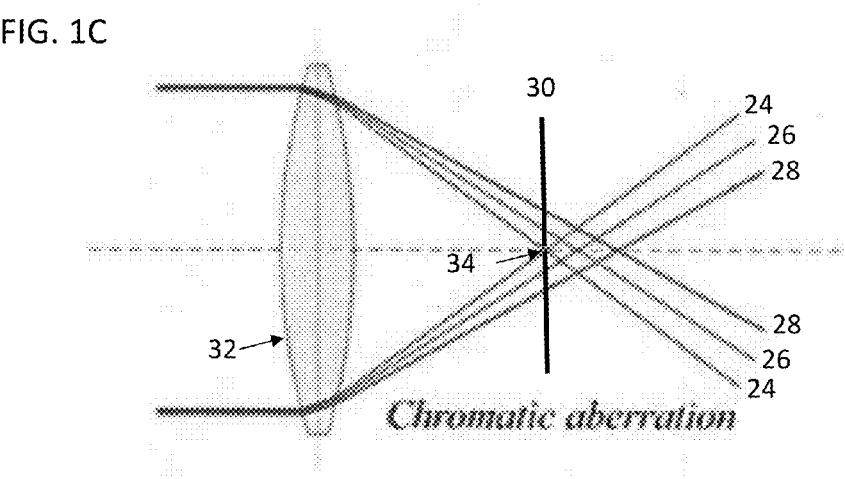
FIG. 1C illustrates the impact of chromatic aberration on optical detection systems. Light paths and focal lengths/points for three different wavelengths of light (line pairs 24, 26, and 28) collected by lens 32. The focal length is where the like-numbered lines cross (sometimes called the focal point). Due to chromatic aberration, when an aperture 30 that blocks the passage of non-core region light of wavelength 24 (the opening in the aperture is indicated by 34) is placed between the light collection system and a detector (not shown), it will block significant portions of light in other wavelengths (e.g., lines 26 and 28) which negatively impacts their detection, e.g., using additional detectors/light conveyors.

In certain embodiments, the optical detection system is configured to collect and detect wavelengths of light other than SSC wavelength light. As is known in the art, the focal length of different wavelengths of light collected and imaged by a light collection system, e.g., with an objective lens assembly, are often different form each other. This phenomenon is referred to as chromatic aberration and is schematized in FIG. 1C. This figure shows the light paths and focal lengths/points for three different wavelengths of light collected by lens 32 (with the wavelengths of light represented by pairs of lines 24, 26, and 28; the focal length is where the like-numbered lines cross; sometimes called the focal point). Due to chromatic aberration, when an aperture 30 that blocks the passage of non-core region light of wavelength 24 (the opening in the aperture is indicated by 34) is placed between the light collection system and the detector (not shown), it will block significant portions of light in other wavelengths (lines 26 and 28) which negatively impacts their detection, e.g., using additional detectors/light conveyors.

Therefore, in certain embodiments, the optical mask of the aperture selectively blocks SSC wavelength light from the objective lens imaged collected light that is outside of a core region from reaching the detector. By "selectively blocks" is meant that the optical mask does not block passage of at least one non-SSC wavelength light, including at least 2, at least 3, at least 4, at least 5, at least 6, at least 7, at least 8, at least 9, at least 10, at least 15, at least 20, at least 30, at least 40, at least 50 or more wavelengths of light. In certain embodiments, the optical mask of the aperture only blocks passage of SSC wavelength light. Thus, in certain embodiments, the optical mask element of the aperture functions in a manner similar to optical (or bandpass) filters, which are used in a wide variety of light detection applications (and described in further detail below).

In certain embodiments, the non-SSC wavelength light is light that is emitted from a particle in the flow stream, e.g., a cell or a sub-cellular particle. The light may be emitted from the particle itself and/or from a constituent on or in the particle that has light emitting properties, e.g., a fluorescent molecule. Such embodiments include cells or particles that are bound to fluorescently tagged antibodies and/or that are associated with or express a fluorescent protein. No limitation in this regard is intended.

In certain embodiments, the optical detection system further includes a light dispersion (or separator) module that processes objective lens imaged collected light before being transmitted to one or more detectors. A light dispersion/separator module refers to a device that separates polychromatic light into its component wavelengths (as such, these modules are sometimes referred to as "wavelength separators"). Wavelength separation, according to certain embodiments, may include selectively passing or blocking specific wavelengths or wavelength ranges of the polychromatic light. Light dispersion devices of interest include but are not limited to, colored glass, bandpass filters, interference filters, dichroic mirrors, diffraction gratings, monochromators and combinations thereof, among other wavelength separating devices. In certain instances, the light dispersion module includes one or more bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In certain embodiments, the optical detection system further includes a light conveyer positioned between the aperture and the detector, where the light conveyor is configured to convey objective lens imaged collected light that has passed through the aperture to the detector. In some embodiments, the light conveyer is a fiber optic light conveyor. In certain embodiments, the light conveyor is positioned between a light dispersion module and a detector. Further, multiple light conveyors may be present in the optical detection system, with each light conveyor associated with a corresponding (different) detector. For example, an optical detection system as described herein can have a light conveyor and a detector configured to detect each different wavelength of light that is processed (or separated) by the light dispersion module. In embodiments in which the light conveyor is a fiber optic, the core diameter of the fiber optic (which is the light conveying portion of the fiber optic) is larger than the diameter of the core region of the collected SSC light that is passed through the aperture. Thus, the aperture functions to prevent SSC wavelength light that is outside of the core region from being conveyed by the light conveyor to the detector, thus reducing the optical noise in the SSC wavelength collected light.

Any convenient detector for detecting imaged collected light may be used in the optical detection systems described herein. Detectors of interest may include, but are not limited to, optical sensors or photodetectors, such as active-pixel sensors (APSs), avalanche photodiodes, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes (PMTs), phototransistors, quantum dot photoconductors or photodiodes and combinations thereof, among other photodetectors. In certain embodiments, the collected light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors.

In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera. Where the collected light is measured with a CCD, the active detecting surface area of the CCD may vary, such as from 0.01 $cm^2$ to 10 $cm^2$, such as from 0.05 $cm^2$ to 9 $cm^2$, such as from, such as from 0.1 $cm^2$ to 8 $cm^2$, such as from 0.5 $cm^2$ to 7 $cm^2$ and including from 1 $cm^2$ to 5 $cm^2$.

The number of photodetectors in the subject systems may vary, as desired. For example, the subject systems may include one photodetector or more, such as two photodetectors or more, such as three photodetectors or more, such as four photodetectors or more, such as five photodetectors or more and including ten photodetectors or more. In certain embodiments, systems include one photodetector. In other embodiments, systems include two photodetectors.

Where the subject systems include more than one photodetector, each photodetector may be the same, or the collection of two or more photodetectors may be a combination of different types of photodetectors. For example, where the subject systems include two photodetectors, in some embodiments the first photodetector is a CCD-type device and the second photodetector (or imaging sensor) is a CMOS-type device. In other embodiments, both the first and second photodetectors are CCD-type devices. In yet other embodiments, both the first and second photodetectors are CMOS-type devices. In still other embodiments, the first photodetector is a CCD-type device and the second photodetector is a photomultiplier tube (PMT). In still other embodiments, the first photodetector is a CMOS-type device and the second photodetector is a photomultiplier tube. In yet other embodiments, both the first and second photodetectors are photomultiplier tubes.

In embodiments of the present disclosure, detectors of interest are configured to measure collected light at one or more wavelengths, such as at 2 or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring light emitted by a sample in the flow stream at 400 or more different wavelengths. In some embodiments, 2 or more detectors in an optical detection system as describe herein are configured to measure the same or overlapping wavelengths of collected light (discussed further below).

In some embodiments, detectors of interest are configured to measure collected light over a range of wavelengths (e.g., 200 nm-1000 nm). In certain embodiments, detectors of interest are configured to collect spectra of light over a range of wavelengths. For example, systems may include one or more detectors configured to collect spectra of light over one or more of the wavelength ranges of 200 nm-1000 nm. In yet other embodiments, detectors of interest are configured to measure light emitted by a sample in the flow stream at one or more specific wavelengths. For example, systems may include one or more detectors configured to measure light at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, one or more detectors may be configured to be paired with specific fluorophores, such as those used with the sample in a fluorescence assay.

In embodiments, the detector is configured to measure light continuously or in discrete intervals. In some instances, detectors of interest are configured to take measurements of the collected light continuously. In other instances, detectors of interest are configured to take measurements in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Additional aspects of the disclosure are drawn to optical detection systems that include a light collection system configured to produce objective lens imaged collected light from a detection zone of a flow cell, a detector configured to receive the objective lens imaged collected light, and an optical filter configured to produce at least a first path and a second path of objective lens imaged collected light in which the first path comprises at least a portion of the SSC wavelength light from the objective lens imaged collected light and is transmitted to the detector, e.g., via a light conveyor.

Examples of light collection systems and detectors that find use in the disclosed optical detections systems are provided above and thus are not repeated here.

In certain embodiments, the optical filter is configured to reflect at least a portion of the SSC wavelength light from objective lens imaged collected light to produce the first path, whereas in other embodiments, the optical filter is configured to pass at least a portion of the SSC wavelength light from objective lens imaged collected light to produce the first path.

Figure 2A:
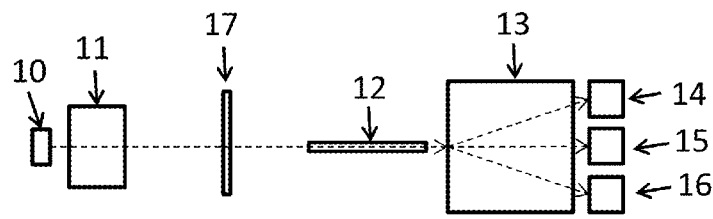
FIG. 2A illustrates a schematic of an embodiment of the disclosure in having an aperture as detailed herein. Designation of elements 10 to 16 are as in FIG. 1A. In this embodiment, collected imaged light (dotted-line arrow shows the light path) is directed through aperture 17 that has an optical mask that selectively blocks SSC wavelength light that is outside of a core region from reaching SSC detector 16 (through fiber optic light conveyor 12 and light dispersion module 13). The optical mask does not block fluorescent wavelengths of light detected by fluorescence detectors 14 and 15.

FIG. 2A provides a schematic of an embodiment of the disclosure in having an aperture as detailed herein (note that the designation of elements 10 to 16 are as in FIG. 1A.) In this figure, collected imaged light (dotted-line arrow shows the light path) is directed through aperture 17 that has an optical mask that selectively blocks SSC wavelength light that is outside of a core region from reaching SSC detector 16 (through fiber optic light conveyor 12 and light dispersion module 13). The optical mask does not block fluorescent wavelengths of light detected by fluorescence detectors 14 and 15. Aperture 17 thus serves to reduce the noise in SSC wavelength light while not affecting wavelengths of light detected by detectors 14 and 15. It is noted that in certain embodiments, only one additional wavelength of light is detected other than the SSC wavelength, and thus only a single additional detector is used (i.e., detector 14 or detector 15, not both).

Figure 2B:
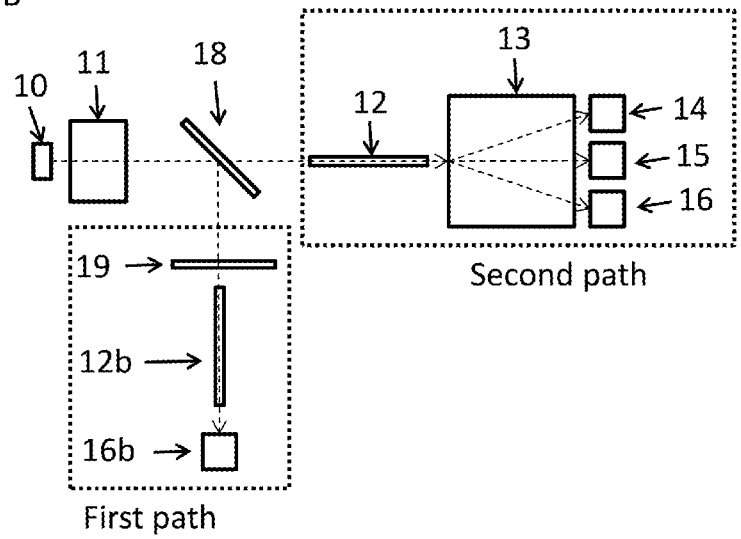
FIG. 2B illustrates a schematic of an embodiment of the disclosure that includes an optical filter configured to generate a first path and a second path of collected imaged light. Collected imaged light (dotted-line arrow shows the light path) is directed to an optical filter 18 that is configured to reflect at least a portion of SSC wavelength light to form first path light while allowing other wavelengths of light to pass through to form a second path (the first and second paths are denoted by the dotted-line boxes). The first path (in this case the reflected path of light from optical filter 18) is directed through aperture 19 that blocks SSC wavelength light that is outside of a core region from reaching SSC detector 16b (through fiber optic light conveyor 12b). Note that in this embodiment, aperture 19 can block all light, as the additional wavelengths of light are detected in the second path. Further, SSC wavelength light that was not diverted to the first path is detected by the separate SSC wavelength detector 16 in the second path (as in FIGS. 1A and 2A). This configuration allows for dual SSC wavelength detection as detailed herein.

FIG. 2B provides a schematic of an embodiment of the disclosure in which an optical filter is configured to reflect at least a portion of the SSC wavelength light from the objective lens imaged collected light to the detector. In this figure, collected imaged light is directed to an optical filter 18 that is configured to reflect at least a portion of SSC wavelength light to form a first path of light while allowing other wavelengths of light to pass through to form a second path. In certain embodiments, the portion of SSC wavelength light that is not reflected into the first path passes through optical filter 18 as part of the second path. The first path is then directed through aperture 19 which blocks SSC wavelength light that is outside of a core region from reaching SSC detector 16b (through fiber optic light conveyor 12b). Note that in this embodiment, aperture 19 can block all light, as the additional wavelengths of light are detected in the second path. Further, SSC wavelength light that was not diverted to the first path is detected by the separate SSC wavelength detector 16 in the second path (as in FIGS. 1A and 2A). This configuration allows for dual SSC wavelength detection as detailed herein.

It is noted here that embodiments in which the optical filter is configured to pass a portion of the SSC wavelength light from the objective lens imaged collected light to form the first path (rather than reflect it) are also contemplated. Thus, in certain embodiments, collected imaged light is directed to an optical filter that is configured to pass at least a portion of SSC wavelength light to form a first path of collected light while reflecting other wavelengths of light to form a second path. In certain embodiments, the portion of SSC wavelength light that is not passed through the optical filter (i.e., part of the first path) is reflected by the optical filter as part of the second path. The first path is then directed to a detector as described for the first path in FIG. 2B.

Figure 2C:
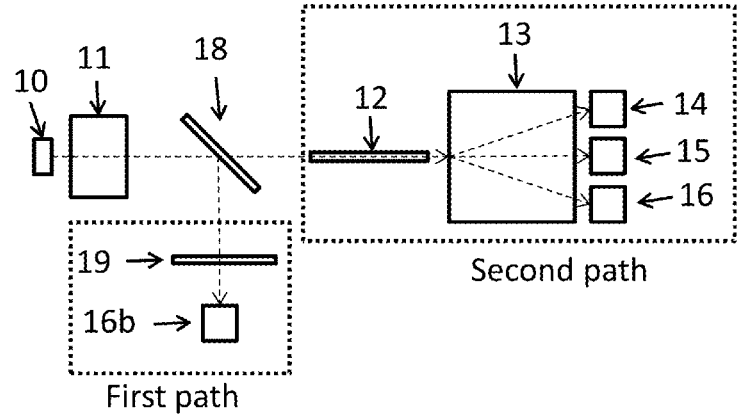
FIG. 2C illustrates a schematic of an additional embodiment similar to that shown in FIG. 2B except that the first path of SSC wavelength light is sent directly to detector 16b (i.e., the light conveyor element 12b of FIG. 2B is eliminated in this embodiment).

FIG. 2C illustrates a schematic of an additional embodiment similar to that shown in FIG. 2B except that the first path of SSC wavelength light is sent directly to detector 16b (i.e., the light conveyor element 12b of FIG. 2B is eliminated in this embodiment).

Figure 3:
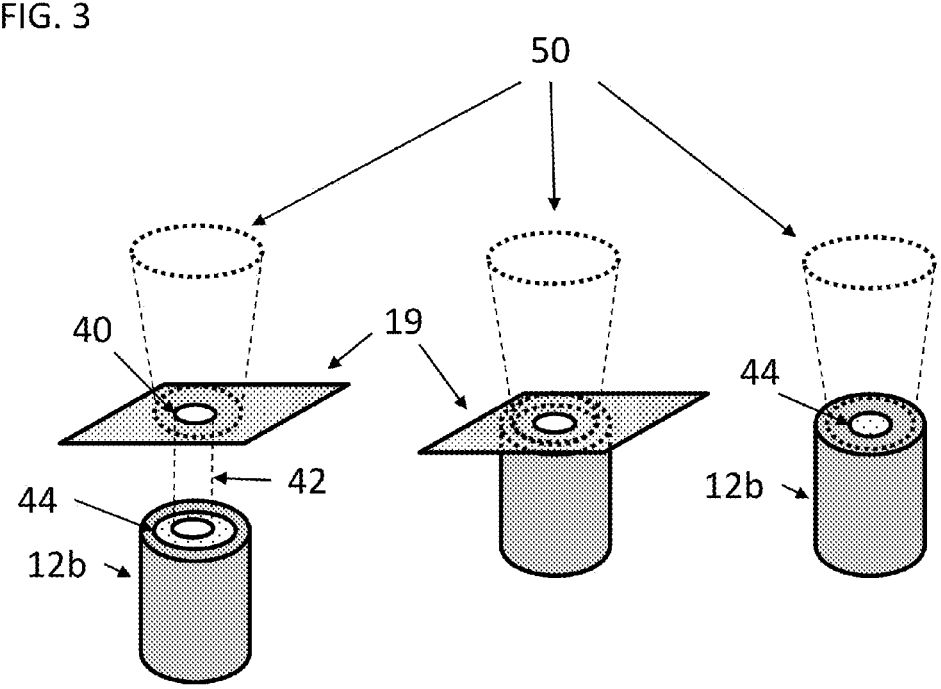
FIG. 3 illustrates representative examples of three configurations of light detection in a first path of light from an optical filter. Element 50 represents the incoming first path of light that includes at least a portion of collected SSC wavelength light. In the left panel, first path (i.e., a portion of SSC wavelength light) is directed through an aperture element 19 that blocks passage of the first path light that is outside of a core region from reaching the detector. The portion of the aperture element through which the first path of light passes 40 is the diameter of the core region. The core region of the first path 42 (i.e., the light that passes through 40) is either detected directly (not shown) or is conveyed by a light conveyor 12b, in this case a fiber optic light conveyor having a core 44 (i.e., the light conveying surface) that has diameter that is larger than the core region. In the middle panel, the aperture element 19 is placed directly on (is attached directly to) the light conveyor (or to the detector; not shown). In such embodiments, the light conveyor/detector can be said to be positioned directly behind the aperture. In the right panel, the light conveyor 12b is configured such that its core 44 is the size of the core region of the first path of light, and thus an aperture element is not required. In some embodiments, the detector has a light detection region that is the size of the core region, and thus an aperture is not required (not shown).

FIG. 3 illustrates representative examples of three configurations of light detection in a first path of light from an optical filter. Element 50 represents the incoming first path of light that includes at least a portion of collected SSC wavelength light. In the left panel, first path (i.e., a portion of SSC wavelength light) is directed through an aperture element 19 that blocks passage of the first path light that is outside of a core region from reaching the detector. The portion of the aperture element through which the first path of light passes 40 is the diameter of the core region. The core region of the first path 42 (i.e., the light that passes through 40) is either detected directly (not shown) or is conveyed by a light conveyor 12b, in this case a fiber optic light conveyor having a core 44 (i.e., the light conveying surface) that has diameter that is larger than the core region. In the middle panel, the aperture element 19 is placed directly on (is attached directly to) the light conveyor (or to the detector; not shown). In such embodiments, the light conveyor/detector can be said to be positioned directly behind the aperture. In the right panel, the light conveyor 12b is configured such that its core 44 is the size of the core region of the first path of light, and thus an aperture element is not required. In some embodiments, the detector has a light detection region that is the size of the core region, and thus an aperture is not required (not shown).

In certain embodiments, the first path contains from 50% to 99% of the of objective lens imaged collected SSC wavelength light, including from 55% to 98%, from 60% to 96%, from 70% to 94%, from 80% to 92%, from 85% to 90%, and any range therebetween. Thus, in certain embodiments the first path comprises at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, and at least about 99% of the objective lens imaged collected SSC wavelength light.

As noted above, the optical filter can be configured such that the first path is produced by light reflected by the optical filter or can be configured such that the first path is produced by light that passes through the optical filter.

In certain embodiments, the optical detection system includes a second detector configured to receive SSC wavelength light that is in the second path of objective lens imaged collected light. In certain of these embodiments, the optical detection system is configured such that the second detector detects both core and non-core region SSC wavelength light. In such embodiments, the optical detection system can detect sub-cellular particles using the first detector (core region SSC wavelength light in the first path) and larger particles (e.g., cells) using the second detector. In certain of these embodiments, a higher portion of objective lens collected SSC wavelength light is present in the first path as compared to the second path, e.g., where the first path comprises about 99% of objective lens collected SSC wavelength light and the second path comprises about 1% of objective lens collected SSC wavelength light; where the first path comprises about 98% of objective lens collected SSC wavelength light and the second path comprises about 2% of objective lens collected SSC wavelength light; where the first path comprises about 97% of objective lens collected SSC wavelength light and the second path comprises about 3% of objective lens collected SSC wavelength light; where the first path comprises about 96% of objective lens collected SSC wavelength light and the second path comprises about 4% of objective lens collected SSC wavelength light; where the first path comprises about 95% of objective lens collected SSC wavelength light and the second path comprises about 5% of objective lens collected SSC wavelength light; where the first path comprises about 90% of objective lens collected SSC wavelength light and the second path comprises about 10% of objective lens collected SSC wavelength light; where the first path comprises about 80% of objective lens collected SSC wavelength light and the second path comprises about 20% of objective lens collected SSC wavelength light; where the first path comprises about 70% of objective lens collected SSC wavelength light and the second path comprises about 30% of objective lens collected SSC wavelength light; where the first path comprises about 60% of objective lens collected SSC wavelength light and the second path comprises about 40% of objective lens collected SSC wavelength light; where the first path comprises about 51% of objective lens collected SSC wavelength light and the second path comprises about 49% of objective lens collected SSC wavelength light. (It is noted that any optical loss from the use of an optical filter is excluded in the above figures.)

In certain embodiments, the optical filter is configured such that the second path includes at least one non-SSC wavelength of collected light. For example, the second path can include non-SSC wavelength light that is emitted from a particle in the flow stream, for example a sub-cellular particle or a cell. Examples of non-SSC wavelengths of light and their detection are provided above and thus not repeated here.

Aspects of the present disclosure provide a system for measuring light emitted by a sample, where the system includes a light source, a flow cell having a detection zone, and an optical detection system of the present disclosure. As detailed above, optical detection systems of the present disclosure include a core region selective side scatter (SSC) collection module of the present disclosure. Core region SSC collection modules are configured to allow for the selective detection SSC wavelength light from a core region of collected light. Any configuration of core region SSC collection modules described above can be employed.

In certain aspects, the optical detection system of the system for measuring light emitted by a sample includes a core region selective SSC collection module that has one or more elements that alone or in combination allow for selective detection of the core region of objective lens imaged collected SSC wavelength light. Such elements can be selected from: one or more apertures having an optical mask that selectively blocks passage of SSC light that is outside of the core region, one or more optical filters, one or more light conveying elements, one or more detectors, and any combination thereof.

Therefore, in certain embodiments, a system for measuring light emitted by a sample is provided that includes: a light source, a flow cell having a detection zone, a light collection system configured to produce objective lens imaged collected light from a detection zone of a flow cell, a detector configured to receive the objective lens imaged collected light, and an aperture positioned between the light collection system and the detector, where the aperture includes an optical mask configured to block SSC wavelength light from the objective lens imaged collected light that is outside of a core region from reaching the detector. The aperture thus has a size (defined by the optical mask) that is matched to the core region of the objective lens imaged collected light. In certain embodiments, the system for measuring light emitted by a sample is configured to collect and detect wavelengths of light other than SSC wavelength light. Thus, in some embodiments, the optical mask of the aperture does not block passage of at least one non-SSC wavelength light. Such embodiments are described in detail above and thus are not repeated here.

Additional aspects of the disclosure are drawn to a system for measuring light emitted by a sample that includes: a light source, a flow cell having a detection zone, a light collection system configured to produce objective lens imaged collected light from a detection zone of a flow cell, a detector configured to receive the objective lens imaged collected light, and an optical filter configured to produce at least a first path and a second path of objective lens imaged collected light in which the first path comprises at least a portion of the SSC wavelength light from the objective lens imaged collected light and is transmitted to the detector, e.g., via a light conveyor.

In certain embodiments, the optical filter is configured to reflect at least a portion of the SSC wavelength light from objective lens imaged collected light to produce the first path, whereas in other embodiments, the optical filter is configured to pass at least a portion of the SSC wavelength light from objective lens imaged collected light to produce the first path. Such embodiments are described in detail above and thus are not repeated here.

In embodiments, the light source of the system for measuring light emitted by a sample may be any suitable broadband or narrow band source of light. Depending on the components in the sample (e.g., cells, beads, non-cellular particles, etc.), the light source may be configured to emit wavelengths of light that vary, ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a narrow band light source emitting a wavelength ranging from 200 nm to 900 nm. For example, the light source may be a narrow band LED (1 nm-25 nm) emitting light having a wavelength ranging between 200 nm to 900 nm. In some embodiments, the light source is a laser, such as continuous wave laser. For example, the laser may be a helium-neon (HeNe) laser. In certain embodiments, the light source is a laser in a flow cytometer.

In other embodiments, the light source is a non-laser light source, such as a lamp, including but not limited to a halogen lamp, deuterium arc lamp, xenon arc lamp, a light-emitting diode, such as a broadband LED with continuous spectrum, superluminescent emitting diode, semiconductor light emitting diode, wide spectrum LED white light source, an multi-LED integrated. In some instances the non-laser light source is a stabilized fiber-coupled broadband light source, white light source, among other light sources or any combination thereof.

The light source may be positioned any suitable distance from the sample (e.g., the flow stream in a flow cytometer), such as at a distance of 0.001 mm or more from the flow stream, such as 0.005 mm or more, such as 0.01 mm or more, such as 0.05 mm or more, such as 0.1 mm or more, such as 0.5 mm or more, such as 1 mm or more, such as 5 mm or more, such as 10 mm or more, such as 25 mm or more and including at a distance of 100 mm or. In addition, the light source irradiate the sample at any suitable angle (e.g., relative the vertical axis of the flow stream), such as at an angle ranging from 10° to 90°, such as from 15° to 85°, such as from 20° to 80°, such as from 25° to 75° and including from 30° to 60°, for example at a 90° angle.

The light source may be configured to irradiate the sample continuously or in discrete intervals. In some instances, systems include a light source that is configured to irradiate the sample continuously, such as with a continuous wave laser that continuously irradiates the flow stream at the interrogation point in a flow cytometer. In other instances, systems of interest include a light source that is configured to irradiate the sample at discrete intervals, such as every 0.001 milliseconds, every 0.01 milliseconds, every 0.1 milliseconds, every 1 millisecond, every 10 milliseconds, every 100 milliseconds and including every 1000 milliseconds, or some other interval. Where the light source is configured to irradiate the sample at discrete intervals, systems may include one or more additional components to provide for intermittent irradiation of the sample with the light source. For example, the subject systems in these embodiments may include one or more laser beam choppers, manually or computer controlled beam stops for blocking and exposing the sample to the light source.

In certain embodiments, the subject systems include flow cytometer systems employing flow cell nozzles and optics subsystems for detecting light emitted by a sample in a flow stream. Suitable flow cytometer systems and methods for analyzing samples include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. *J Pathol*, 2010 December; 222(4):335-344; and Herbig, et al. (2007) *Crit Rev Ther Drug Carrier Syst.* 24(3): 203-255; the disclosures of which are incorporated herein by reference. In certain instances, flow cytometry systems of interest include BD Biosciences FACSCanto™ flow cytometer, BD Biosciences FACSVantage™, BD Biosciences FACSort™, BD Biosciences FACSCount™, BD Biosciences FACScan™, and BD Biosciences FACSCalibur™ systems, a BD Biosciences Influx™ cell sorter, BD Biosciences Jazz™ cell sorter and BD Biosciences Aria™ cell sorter or the like.

In certain embodiments, the subject systems are flow cytometer systems which incorporate one or more components of the flow cytometers described in U.S. Pat. Nos. 3,960,449; 4,347,935; 4,667,830; 4,704,891; 4,770,992; 5,030,002; 5,040,890; 5,047,321; 5,245,318; 5,317,162; 5,464,581; 5,483,469; 5,602,039; 5,620,842; 5,627,040; 5,643,796; 5,700,692; 6,372,506; 6,809,804; 6,813,017; 6,821,740; 7,129,505; 7,201,875; 7,544,326; 8,140,300; 8,233,146; 8,753,573; 8,975,595; 9,092,034; 9,095,494 and 9,097,640; the disclosures of which are herein incorporated by reference.

Methods for Measuring Light Emitted by a Sample

Aspects of the disclosure include methods for measuring light emitted from a sample. In certain embodiments, the light emitted by the sample is collected and measured using an optical detection system having a core region SSC collection module as described herein.

In certain embodiments, methods of analyzing a flow stream are provided, where the method includes: irradiating a flow stream with a light source, generating objective lens imaged light collected from a detection zone of the irradiated flow stream, and passing the objective lens imaged collected light through a core region SSC collection module to a detector, where the core region SSC collection module selectively blocks side scatter (SSC) wavelength light outside of a core region from reaching the detector, thereby analyzing the flow stream.

The sample analyzed can be any sample that is of interest to a user. In certain embodiments, the sample contains a biological component, or is a biological sample. The term "biological sample" is used in its conventional sense to refer to a sample derived from or containing a whole organism, e.g., a prokaryotic cells, eukaryotic cells, plants, fungi or a subset of animal tissues, cells or component parts which may in certain instances be found in blood, mucus, lymphatic fluid, synovial fluid, cerebrospinal fluid, saliva, bronchoalveolar lavage, amniotic fluid, amniotic cord blood, urine, vaginal fluid and semen. As such, a "biological sample" refers to both the native organism or a subset of its tissues as well as to: a homogenate; isolated, purified or enriched biological particles (e.g., DNA, RNA, proteins, sub-cellular organelles, etc.); and lysates or extracts prepared from the organism or a subset of its tissues, including but not limited to, for example, plasma, serum, spinal fluid, lymph fluid, sections of the skin, respiratory, gastrointestinal, cardiovascular, and genitourinary tracts, tears, saliva, milk, blood cells, tumors, organs. Biological samples may be any type of organismic tissue, including both healthy and diseased tissue (e.g., cancerous, malignant, necrotic, etc.). In certain embodiments, the biological sample is a liquid sample, such as blood or derivative thereof, e.g., plasma, tears, urine, semen, etc., where in some instances the sample is a blood sample, including whole blood, such as blood obtained from venipuncture or fingerstick (where the blood may or may not be combined with any reagents prior to assay, such as preservatives, anticoagulants, etc.).

In certain embodiments the source of the sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While embodiments of the present disclosure may be applied to samples from a human subject, it is to be understood that the methods may also be carried-out on samples from other animal subjects (that is, in "non-human subjects") such as, but not limited to, birds, mice, rats, dogs, cats, livestock and horses.

In practicing methods according to certain embodiments, a sample (e.g., in a flow stream of a flow cytometer) is irradiated with light from a light source. Any convenient light source may be employed. For example, in some embodiments, the sample is irradiated with a broadband light source, which emits light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. In other embodiments, methods includes irradiating with a narrow band light source emitting a particular wavelength or a narrow range of wavelengths, such as for example with a light source which emits light in a narrow range of wavelengths like a range of 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Where methods include irradiating with a narrow band light source, narrow band light source protocols of interest may include, but are not limited to, a narrow wavelength LED, laser diode or a broadband light source coupled to one or more optical bandpass filters, diffraction gratings, monochromators or any combination thereof. In certain embodiments, the methods include irradiating the sample with one or more lasers, where the type and number of lasers will vary depending on the sample as well as desired light collected. As such, the laser or lasers can be selected from: one or more gas lasers, one or more dye lasers, one or more excimer lasers, one or more metal-vapor lasers, one or more solid-state lasers, and combinations thereof.

The sample may be irradiated with one or more of the above mentioned light sources, such as two or more light sources, such as three or more light sources, such as four or more light sources, such as five or more light sources and including ten or more light sources. The light source may include any combination of types of light sources. For example, in some embodiments, the methods include irradiating the sample in the flow stream with an array of lasers, such as an array having one or more gas lasers, one or more dye lasers and one or more solid-state lasers.

The sample may be irradiated with wavelengths ranging from 200 nm to 1500 nm, such as from 250 nm to 1250 nm, such as from 300 nm to 1000 nm, such as from 350 nm to 900 nm and including from 400 nm to 800 nm. For example, where the light source is a broadband light source, the sample may be irradiated with wavelengths from 200 nm to 900 nm. In other instances, where the light source includes a plurality of narrow band light sources, the sample may be irradiated with specific wavelengths in the range from 200 nm to 900 nm. For example, the light source may be plurality of narrow band LEDs (1 nm-25 nm) each independently emitting light having a range of wavelengths between 200 nm to 900 nm. In other embodiments, the narrow band light source includes one or more lasers (such as a laser array) and the sample is irradiated with specific wavelengths ranging from 200 nm to 700 nm, such as with a laser array having gas lasers, excimer lasers, dye lasers, metal-vapor lasers and solid-state laser as described above.

Where more than one light source is employed, the sample may be irradiated with the light sources simultaneously or sequentially, or a combination thereof. For example, the sample may be simultaneously irradiated with both light sources. In other embodiments, the flow stream is sequentially irradiated with both light sources. Where two light sources irradiate sequentially, the time each light source irradiates the sample may independently be 0.001 microseconds or more, such as 0.01 microseconds or more, such as 0.1 microseconds or more, such as 1 microsecond or more, such as 5 microseconds or more, such as 10 microseconds or more, such as 30 microseconds or more and including 60 microseconds or more. For example, methods may include irradiating the sample with the light source (e.g., laser) for a duration which ranges from 0.001 microseconds to 100 microseconds, such as from 0.01 microseconds to 75 microseconds, such as from 0.1 microseconds to 50 microseconds, such as from 1 microsecond to 25 microseconds and including from 5 microseconds to 10 microseconds. In embodiments where sample is sequentially irradiated with two or more light sources, the duration sample is irradiated by each light source may be the same or different.

The sample may be irradiated continuously or in discrete intervals. In some instances, methods include irradiating the sample with the light source continuously. In other instances, the sample is irradiated with the light source in discrete intervals, such as irradiating every 0.001 millisecond, every 0.01 millisecond, every 0.1 millisecond, every 1 millisecond, every 10 milliseconds, every 100 milliseconds and including every 1000 milliseconds, or some other interval.

Depending on the light source, the sample may be irradiated from a distance which varies such as 0.01 mm or more, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more. Also, the angle or irradiation may also vary, ranging from 10° to 90°, such as from 15° to 85°, such as from 20° to 80°, such as from 25° to 75° and including from 30° to 60°, for example at a 90° angle.

In certain embodiments, the light emitted by the irradiated sample is processed by a light collection system, e.g., an objective lens assembly, and measured by an optical detection system having a core region SSC collection module as describe above.

Therefore, in certain embodiments, the methods include collecting light emitted from the irradiated sample (e.g., from a detection zone of an irradiated flow stream) and generating objective lens imaged light therefrom. In certain aspects, generating objective lens imaged light includes passing the collected light through one or more objective lenses, which may include one or a combination of a collimating lens, a focusing lens, a magnifying lens, a de-magnifying lens, or other lens, that are configured to receive collected light (e.g., from a detection zone of a flow cell) and produce imaged light.

In certain embodiments, the method includes passing the objective lens imaged collected light through an aperture to a detector, where the aperture has an optical mask that blocks SSC wavelength light outside of a core region from reaching the detector. (This aspect of the disclosed methods can be described as blocking SSC wavelength light that is outside of a core region from reaching the detector.) As described above, in certain embodiments, the core region of the objective lens imaged collected SSC wavelength light has a diameter ranging from 50 microns(μ) to 500μ, including form 70μ to 450μ, form 70μ to 400μ, form 100μ to 400μ, form 200μ to 400μ, etc. As such, in certain embodiments, the core region has a diameter of or about 500μ, of or about 475μ, of or about 450μ, of or about 425μ, of or about 400μ, of or about 375μ, of or about 350μ, of or about 325μ, of or about 300μ, of or about 275μ, of or about 250μ, of or about 225μ, of or about 200μ, of or about 175μ, of or about 150μ, of or about 125μ, of or about 100μ, of or about 75μ, of or about 50μ, or anywhere in between.

In certain embodiments, the optical mask of the aperture selectively blocks SSC wavelength light from the objective lens imaged collected light that is outside of a core region from reaching the detector. By "selectively blocks" is meant that the optical mask does not block passage of at least one non-SSC wavelength light, including at least 2, at least 3, at least 4, at least 5, at least 6, at least 7, at least 8, at least 9, at least 10, at least 15, at least 20, at least 30, at least 40, at least 50 or more wavelengths of light. In certain embodiments, the optical mask of the aperture only blocks passage of SSC wavelength light. Thus, in certain embodiments, the optical mask element of the aperture functions in a manner similar to optical filters (or bandpass filters), which are used in a wide variety of light detection applications.

In certain embodiments, the method includes detecting one or more non-SSC wavelengths of light that pass through the optical mask of the aperture by one or more additional detectors (e.g., a second detector, a third detector, etc.). In certain embodiments, the one or more non-SSC wavelengths of light is light that is emitted from a particle in the flow stream, e.g., a cell or a sub-cellular particle. The light may be emitted from the particle itself and/or from a constituent on or in the particle that has light emitting properties, e.g., a fluorescent molecule. Such embodiments include cells or particles that are bound to fluorescently tagged antibodies and/or that are associated with or express a fluorescent protein. No limitation in this regard is intended.

In certain embodiments, the method further includes passing the objective lens imaged collected light through a light dispersion (or separator) module that processes the light before being transmitted to one or more detectors. A light dispersion/separator module refers to a device that separates polychromatic light into its component wavelengths (as such, these modules are sometimes referred to as "wavelength separators"). Wavelength separation, according to certain embodiments, may include selectively passing or blocking specific wavelengths or wavelength ranges of the polychromatic light. Light dispersion devices of interest include but are not limited to, colored glass, bandpass filters, interference filters, dichroic mirrors, diffraction gratings, monochromators and combinations thereof, among other wavelength separating devices. In certain instances, the light dispersion module includes one or more bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm.

In addition to the aspects detailed above, certain embodiments of the disclosed methods include directing the objective lens imaged collected light to an optical filter configured to produce at least a first path and a second path of objective lens imaged collected light. In embodiments, the optical filter is used in place of the aperture having an optical mask that selectively blocks SSC wavelength light as described above. In such cases, the first path of objective lens imaged collected light comprises at least a portion of the SSC wavelength light from the objective lens imaged collected light. In certain embodiments, the optical filter reflects at least a portion of the SSC wavelength light from the objective lens imaged collected light to produce the first path, whereas in other embodiments, the optical filter passes at least a portion of the SSC wavelength light from the objective lens imaged collected light to produce the first path.

In certain embodiments, the first path contains from 50% to 99% of the of objective lens imaged collected SSC wavelength light, including from 55% to 98%, from 60% to 96%, from 70% to 94%, from 80% to 92%, from 85% to 90%, and any range therebetween. Thus, the first path may include at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, or at least about 99% of the objective lens imaged collected SSC wavelength light.

In certain embodiments, the portion of SSC wavelength light that is not in the first path of collected light is present in the second path. In general, a higher portion of objective lens collected SSC wavelength light is present in the first path as compared to the second path, e.g., where the first path comprises about 99% of objective lens collected SSC wavelength light and the second path comprises about 1% of objective lens collected SSC wavelength light; where the first path comprises about 98% of objective lens collected SSC wavelength light and the second path comprises about 2% of objective lens collected SSC wavelength light; where the first path comprises about 97% of objective lens collected SSC wavelength light and the second path comprises about 3% of objective lens collected SSC wavelength light; where the first path comprises about 96% of objective lens collected SSC wavelength light and the second path comprises about 4% of objective lens collected SSC wavelength light; where the first path comprises about 95% of objective lens collected SSC wavelength light and the second path comprises about 5% of objective lens collected SSC wavelength light; where the first path comprises about 90% of objective lens collected SSC wavelength light and the second path comprises about 10% of objective lens collected SSC wavelength light; where the first path comprises about 80% of objective lens collected SSC wavelength light and the second path comprises about 20% of objective lens collected SSC wavelength light; where the first path comprises about 70% of objective lens collected SSC wavelength light and the second path comprises about 30% of objective lens collected SSC wavelength light; where the first path comprises about 60% of objective lens collected SSC wavelength light and the second path comprises about 40% of objective lens collected SSC wavelength light; where the first path comprises about 51% of objective lens collected SSC wavelength light and the second path comprises about 49% of objective lens collected SSC wavelength light.

In certain embodiments, the method further includes directing the first path of objective lens imaged collected light through an aperture to a detector, where the aperture blocks passage of SSC wavelength light that is outside of a core region from reaching the detector (the core region dimensions are described above). In certain embodiments, the core region of the SSC wavelength light in the first path is either detected directly or is conveyed by a light conveyor (e.g., a fiber optic) to the detector, as described in detail above (see, e.g., FIG. 3 and its description). In such embodiments, the light conveyor may have a light conveying surface that has diameter that is larger than the core region of the first path that has passed through the aperture. In some instances, the aperture and the light conveyor (or detector) are in direct contact, while in other embodiments they are not (see, e.g., FIG. 3, left and center panels).

In certain embodiments, the method includes directing the first path of objective lens imaged collected light onto the light conveying surface of a light conveyor that is the size of the core region, e.g., a fiber optic having a core that is the diameter of the core region (see FIG. 3, right panel). In such embodiments, an aperture element is not required. In embodiments without a light conveyor (e.g., a fiber optic), the first path of objective lens imaged collected light is directed to a detector that has a light detecting surface that is the size of the core region.

In certain embodiments, the method includes detecting one or more wavelengths of light in the second path of objective lens imaged collected light by one or more additional detectors (e.g., a second detector, a third detector, etc.). Depending on the configuration of the optical filter that produces the first and second paths, the second path can be objective lens collected light that is reflected by the optical filter or that is passed by the optical filter.

In certain embodiments, the one or more wavelengths of light detected in the second path include at least one non-SSC wavelength light. In certain embodiments, the at least one non-SSC wavelength light is light that is emitted from a particle in the flow stream, e.g., a cell or a sub-cellular particle (e.g., as described above). In certain embodiments, both SSC and non-SSC wavelength light is detected in the second path. As noted above, the SSC wavelength light in the second path is that portion of SSC wavelength light that is not in the first path. In general, the portion of SSC wavelength light in the second path is less than the portion in the first path. When SSC wavelength light is detected separately in both the first and second paths, it can be used to assess different aspects of the sample under interrogation. For example, SSC wavelength light in the first path (which is processed to block non-core region SSC wavelength light from being detected) can be used to identify sub-micron sized particles in the sample being interrogated (e.g., sub-cellular organelles, vesicles, etc.) while the SSC wavelength light in the second path (which is not processed to block non-core region SSC wavelength light from being detected) can be used to identify larger particles in the sample being interrogated.

In certain embodiments, the method further includes passing the second path of objective lens imaged collected light through a light dispersion (or separator) module that processes the light before being transmitted to the one or more detectors (as described above).

In practicing the subject methods, the light propagated through the optical detection system as disclosed herein is measured at one or more wavelengths, such as at 5 or more different wavelengths, such as at 10 or more different wavelengths, such as at 25 or more different wavelengths, such as at 50 or more different wavelengths, such as at 100 or more different wavelengths, such as at 200 or more different wavelengths, such as at 300 or more different wavelengths and including measuring the collected light at 400 or more different wavelengths.

In some embodiments, methods include measuring the collected light over a range of wavelengths (e.g., 200 nm-1000 nm). For example, methods may include collecting spectra of light over one or more of the wavelength ranges of 200 nm-1000 nm. In yet other embodiments, methods include measuring collected light at one or more specific wavelengths. For example, the collected light may be measured at one or more of 450 nm, 518 nm, 519 nm, 561 nm, 578 nm, 605 nm, 607 nm, 625 nm, 650 nm, 660 nm, 667 nm, 670 nm, 668 nm, 695 nm, 710 nm, 723 nm, 780 nm, 785 nm, 647 nm, 617 nm and any combinations thereof. In certain embodiments, methods including measuring wavelengths of light which correspond to the fluorescence peak wavelength of certain fluorophores.

The collected light may be measured continuously or in discrete intervals. In some instances, methods include taking measurements of the light continuously. In other instances, the light is measured in discrete intervals, such as measuring light every 0.001 millisecond, every 0.01 millisecond, every 0.1 millisecond, every 1 millisecond, every 10 milliseconds, every 100 milliseconds and including every 1000 milliseconds, or some other interval.

Measurements of the collected light may be taken one or more times during the subject methods, such 2 or more times, such as 3 or more times, such as 5 or more times and including 10 or more times. In certain embodiments, the light is measured two or more times, with the data in certain instances being averaged.

Light measurements may be taken with any convenient protocol, including but not limited to optical sensors or photodetectors, such as active-pixel sensors (APSs), avalanche photodiode, image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, the transmitted light is measured with a charge-coupled device (CCD), semiconductor charge-coupled devices (CCD), active pixel sensors (APS), complementary metal-oxide semiconductor (CMOS) image sensors or N-type metal-oxide semiconductor (NMOS) image sensors. In certain embodiments, light is measured with a charge-coupled device (CCD). Where the transmitted light is measured with a CCD, the active detecting surface area of the CCD may vary, such as from 0.01 cm$^2$ to 10 cm$^2$, such as from 0.05 cm$^2$ to 9 cm$^2$, such as from, such as from 0.1 cm$^2$ to 8 cm$^2$, such as from 0.5 cm$^2$ to 7 cm$^2$ and including from 1 cm$^2$ to 5 cm$^2$.

Kits

Aspects of the present disclosure further include kits, where kits include a core region selective SSC collection module as described herein. Core region SSC collection modules as describe herein are configured to allow for the selective detection SSC wavelength light from a core region of collected light. As such, the kits can include one or more aperture elements, e.g., for blocking or selectively blocking SSC wavelength light that is outside of a core region, one or more optical filters, one or more light conveying elements, one or more detectors, and any combination thereof. In certain embodiments, the aperture element(s) may have an adjustable aperture for increasing or decreasing the aperture diameter, which will adjust the size of the core region of the SSC wavelength light that passes therethrough. In certain embodiments, a core region selective SSC collection module is configured to be added on to an existing optical detection system, e.g., a flow cytometer, and as such may include hardware for attaching or inserting the module.

The various assay components of the kits may be present in separate containers, or some or all of them may be pre-combined/assembled. For example, an aperture and a fiber optic light conveyor can be pre-assembled and present in a single sealed package.

In addition to the above components, the subject kits may further include (in certain embodiments) instructions, e.g., for adding the core region selective SSC collection module to an optical detection device or for using a system having the core region selective SSC collection module according to aspects of the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

Optical detection systems that include a core region SSC collection module as detailed herein find use in improving the signal-to-noise ratio in SSC detection as compared currently available systems. The disclosed core region SSC collection modules are configured to take into account the chromatic aberration observed with objective lens imaged light that includes multiple wavelengths of light. This allows, for example, for an improvement in the detection of sub-cellular (or sub-micron) sized particles in a sample interrogated in a flow stream, e.g., in a flow cytometer, allowing for improved simultaneous detection and analysis of both sub-micron sized particles and larger particles, e.g., cells.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An optical detection system comprising:
   a light collection system comprising an objective lens and configured to produce objective lens imaged collected light from a detection zone of a flow cell, wherein the objective lens imaged collected light is light collected and focused by the objective lens;
   a light disperser configured to separate the objective lens imaged collected light into at least two wavelengths of light;
   a first detector configured to detect a first of the at least two wavelengths of light and a second detector configured to detect a second of the at least two wavelengths of light, wherein the first wavelength of light is a side scatter (SSC) wavelength light; and
   an aperture comprising an optical mask configured to selectively block SSC wavelength light from the objective lens imaged collected light that is outside of an innermost core region from reaching the first detector, wherein the aperture has a size that is matched to the innermost core region.

2. The optical detection system according to claim 1, wherein the aperture has a diameter ranging from 50μ to 500μ.

3. The optical detection system according to claim 1, wherein the optical mask does not block passage of at least one non-side scatter wavelength light.

4. The optical detection system according to claim 1, further comprising a fiber optic light conveyer positioned between the aperture and the light disperser, wherein the fiber optic light conveyor is configured to convey objective lens imaged collected light that has passed through the aperture to the light disperser.

5. The optical detection system according to claim 4, wherein each of the first and second detectors comprise a photodiode based light detector or a photomultiplier tube (PMT).

6. The optical detection system according to claim 5, wherein the fiber optic light conveyor comprises a core that has a diameter that is larger than the innermost core region.

7. A method of analyzing a flow stream, the method comprising:
  irradiating a flow stream with a light source;
  generating objective lens imaged light collected from a detection zone of the irradiated flow stream, wherein the objective lens imaged collected light is light collected and focused by the objective lens; and
  passing the objective lens imaged collected light through an aperture to a light disperser, wherein:
  (i) the aperture comprises an optical mask that selectively blocks side scatter (SSC) wavelength light outside of an innermost core region from passing through, wherein the aperture has a size that is matched to the innermost core region; and
  (ii) the light disperser is configured to separate the objective lens imaged collected light into at least a first and a second wavelength of light, wherein the first wavelength of light is SSC wavelength light; and
  detecting the first and second wavelengths of light to analyze the flow stream.

* * * * *